(12) United States Patent
Wuestenbecker (10) Patent No.: US 8,575,562 B2
(45) Date of Patent: Nov. 5, 2013

(54) APPARATUS AND SYSTEM FOR INSPECTING AN ASSET

(75) Inventor: Michael Wuestenbecker, Lutjensee (DE)

(73) Assignee: General Electric Company, Schenectady, NY (US)

( * ) Notice: Subject to any disclaimer, the term of this patent is extended or adjusted under 35 U.S.C. 154(b) by 21 days.

(21) Appl. No.: 13/360,350

(22) Filed: Jan. 27, 2012

(65) Prior Publication Data

US 2013/0193338 A1     Aug. 1, 2013

(51) Int. Cl.
*G01J 1/42*         (2006.01)
(52) U.S. Cl.
USPC ......................................................... 250/393
(58) Field of Classification Search
USPC .......................................................... 250/393
See application file for complete search history.

(56) References Cited

U.S. PATENT DOCUMENTS

| 3,088,027 A | 4/1963 | Graham |
| 3,969,153 A | 7/1976 | Suzuki et al. |
| 4,699,485 A | 10/1987 | Lippman et al. |
| 7,427,761 B2 * | 9/2008 | Ohtaka et al. ................. 250/393 |
| 2008/0289421 A1 | 11/2008 | Brignac et al. |

* cited by examiner

*Primary Examiner* — Kiho Kim
(74) *Attorney, Agent, or Firm* — Hiscock & Barclay LLP (57) ABSTRACT

Embodiments of an apparatus, and an inspection system incorporating the apparatus, prevent exposure to radiation during inspection of tubes (e.g., boiler tubes). The embodiments can comprise a housing and a pair of translating baffles that engage the outside of the housing. In one embodiment, the housing moves relative to the translating baffles during rotation of the housing to change the orientation of the housing relative to the boiler tubes. The housing and the translating baffles maintain engagement to prevent radiation from leaking out of the housing and into the surrounding environment.

20 Claims, 13 Drawing Sheets

APPARATUS AND SYSTEM FOR INSPECTING AN ASSET

BACKGROUND OF THE INVENTION

The subject matter disclosed herein relates to inspection and image acquisition and, more particularly, to embodiments of an apparatus and a system for imaging tubes and pipes.

Boiler tube failures are a major cause of forced shutdowns in utility installations, e.g., fossil fuel power plants. As a result of various operational conditions such as heat, pressure, and wear over time, boiler tubes eventually begin to fail by developing circumferential and axial cracks, as well as experience wall thinning (through both erosion and corrosion). When a boiler tube begins to leak, for example, steam escaping through the leak is lost to the boiler operation. Unless the leak is discovered and repaired, the leak may continue to grow until the tube eventually ruptures, thereby forcing the boiler to shut it down immediately. Unplanned shut downs are inconvenient and can be costly and, as such, early boiler tube leak detection methods are highly desirable.

The discussion above is merely provided for general background information and is not intended to be used as an aid in determining the scope of the claimed subject matter.

BRIEF DESCRIPTION OF THE INVENTION

This disclosure describes embodiments of an apparatus, and a system incorporating the apparatus, that can house components of an inspection device to irradiate an asset, e.g., a boiler tube, but that prevents exposure to radiation in the surrounding environment. An advantage that the practice of some embodiments of the apparatus and system is to reduce the footprint of the inspection system and to reduce the amount of materials required to prevent exposure to radiation The present disclosure describes an apparatus for inspecting an asset. The apparatus includes a support structure comprising a base assembly that can rotate, the support structure having support members that hold the asset in position for inspection. The apparatus can also include a housing disposed on the base assembly. The housing can have a first side wall and a second side wall, the first side wall and the second side wall having an aperture exposing the interior of the housing and through which the asset can penetrate the housing for exposure to radiation. The apparatus can also include a pair of translating baffles engaging the first side wall and the second side wall of the housing. In one embodiment, the translating baffles and the housing move relative to one another in response to rotation of the base assembly. In one embodiment, the translating baffles and the housing maintain engagement with one another to form an integrated section in combination with the support members on the first wall and the second wall proximate the asset.

The present disclosure also describes a containment apparatus for housing a radiation source and a detector. The containment apparatus includes a support structure comprising an actuator and an enclosure coupled to the actuator. The enclosure can include a housing with an aperture on opposing side walls and a pair of translating baffles on the outside of the housing forming an integrated section with the housing about the apertures. In one embodiment, the translating baffles and the housing move relative to the one another in response to rotation of the base assembly.

The present disclosure further describes an inspection system for generating images of an asset. The inspection system includes an inspection device comprising a detector element sensitive to radiation from a radiation source. The inspection system also includes an enclosure surrounding the inspection device, the enclosure having a housing and a pair of translating baffles that engage the housing on opposing side walls. The inspection system further includes a support structure supporting the enclosure. The support structure includes a pivot element forming an integrated section with the translating baffles and the housing through which the asset passes from one of the opposing side walls to the other opposing side wall. In one embodiment, the translating baffles and the housing move relative to one another when the housing changes orientation from a first orientation to a second orientation. In one embodiment, the translating baffles, the housing, and the pivot member maintain engagement with one another at the integrated section in each of the first orientation and the second orientation proximate the asset.

This brief description of the invention is intended only to provide a brief overview of the subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
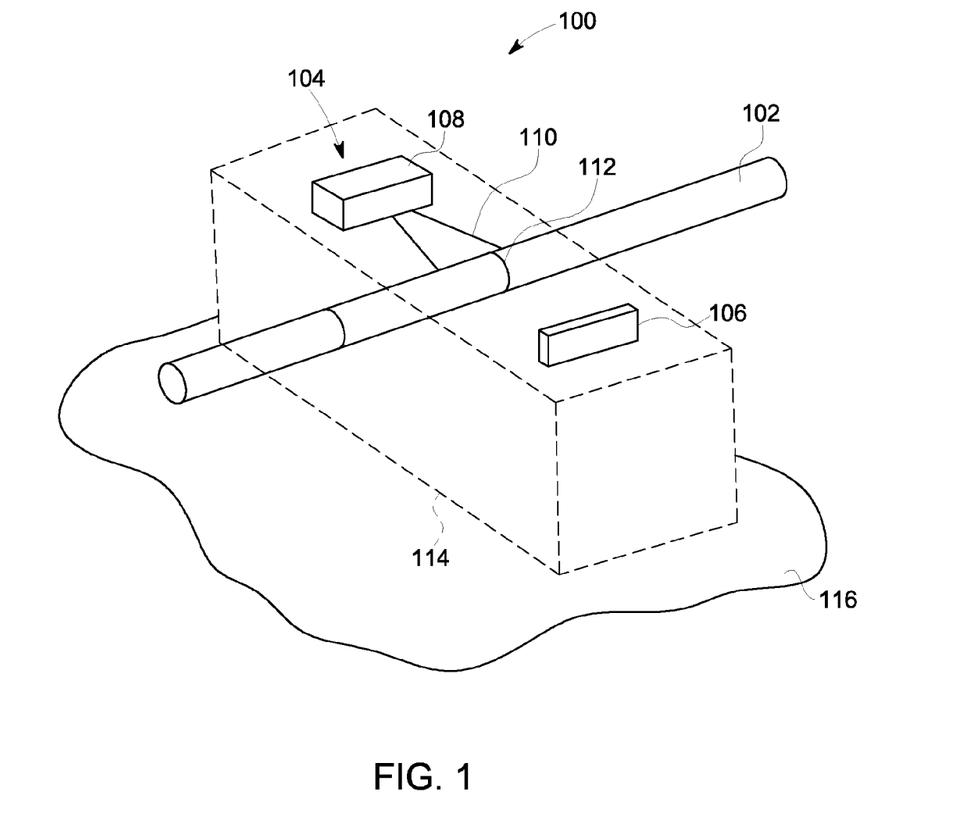
FIG. 1 depicts a perspective view of an exemplary inspection system.

FIG. 1 illustrates an exemplary inspection system 100 for performing non-destructive testing and inspection of an asset 102. Examples of the asset 102 include pipes and tubes that transport fluids (e.g., water and/or steam). These tubes are found in various types of applications, e.g., boilers. In one embodiment, the inspection system includes an inspection device 104 with a detector element 106 and a radiation source 108 that generates and directs radiation 110 toward the asset 102. The detector element 106 can generate electrical signals (e.g., analog and/or digital signals) in response to the radiation 110. An image processor can receive and process these electrical signals to generate an image (e.g., a digital image and/or a digital radiograph).

The resulting image can reveal conditions of the asset, e.g., anomalies found below the exterior surface of the asset 102 and hidden from view. In one example, the radiation 110 impinges on a feature-of-interest 112 on the asset 102, e.g., a weld that couples together two sections of pipe to form a tube. Example of the welds can be found in butt-welded tube joints, e.g., for tubes with a diameter from 25 mm to 110 mm. These welds may contain anomalies, e.g., voids and cracks, that can weaken the connection between the two sections of pipe. However, because detection of these anomalies is often unlikely to occur during visual inspection of the asset 102, implementation of non-destructive inspection and imaging using the inspection system 100 may be necessary to properly diagnose any potential issues and/or potential problems proximate the feature-of-interest 112.

As shown in FIG. 1, the inspection system 100 includes a containment apparatus 114 (also an "apparatus 114") that rests on a surface 116, e.g., a factory floor. The containment apparatus 114 encloses the detector element 106 and the radiation source 108. The asset 102 travels through the containment apparatus 114. Despite the breach in the integrity of the containment apparatus 114, the containment apparatus 114 comprises structure sufficient to prevent the radiation 110 from escaping into the surrounding environment. This feature permits safe operation of the inspection device 102 in lieu of any peripheral containment structure or cabinet to prevent exposure to radiation 110 by personnel (e.g., operators and technicians). Such cabinets often have a footprint that is much larger than the containment apparatus 114, e.g., on the order of 8 m$^3$ or more, which is large enough to enclose the components of the inspection device 104 as well as a large part of the asset 102. To prevent exposure to radiation, the cabinets comprise various materials including lead, steel, and/or concrete to create massive formations that use, for example, on the order of six tons and greater of lead.

Examples of the containment apparatus 114, on the other hand, perform the same functions of the cabinet but in a much smaller and more compact footprint. The features of the containment apparatus 114 reduce the overall footprint of the inspection system 100 and makes the containment apparatus 114 significantly more mobile, e.g., for reorientation within a factory setting and/or for transport to facilitate mobile inspection services on a truck or trailer. The smaller, more compact design also reduces the amount of materials necessary to enclose the inspection device 104 and substantially eliminate exposure to radiation. For example, the containment apparatus 114 may use on the order of only two tons or less of lead. Moreover, despite its small size, the containment apparatus 114 can move (e.g., rotate) the inspection device 104 relative to the asset 102. This feature permits the inspection system 100 to capture images of the asset 102 at different angles and/or orientations to facilitate a more thorough analysis of the feature-of-interest 112.

Figure 2:
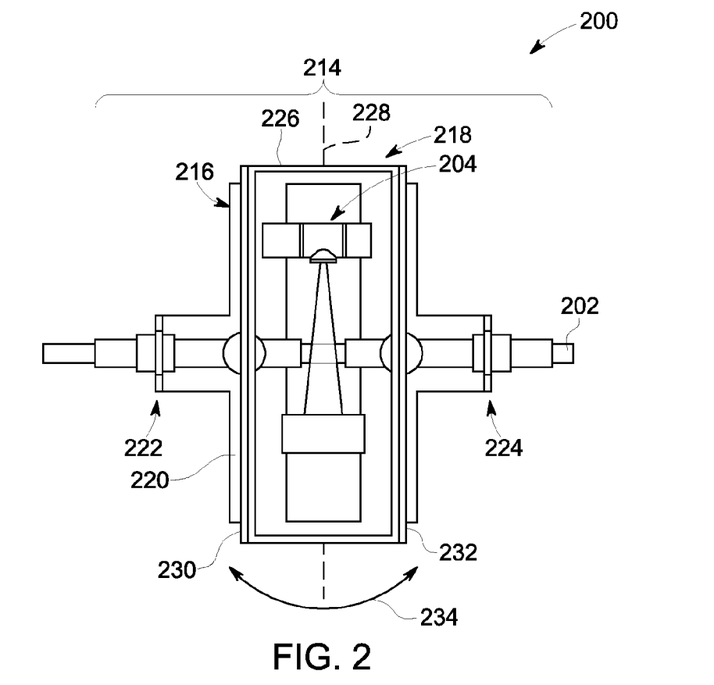
FIG. 2 depicts a top view of an exemplary inspection system in a first orientation.
Figure 3:
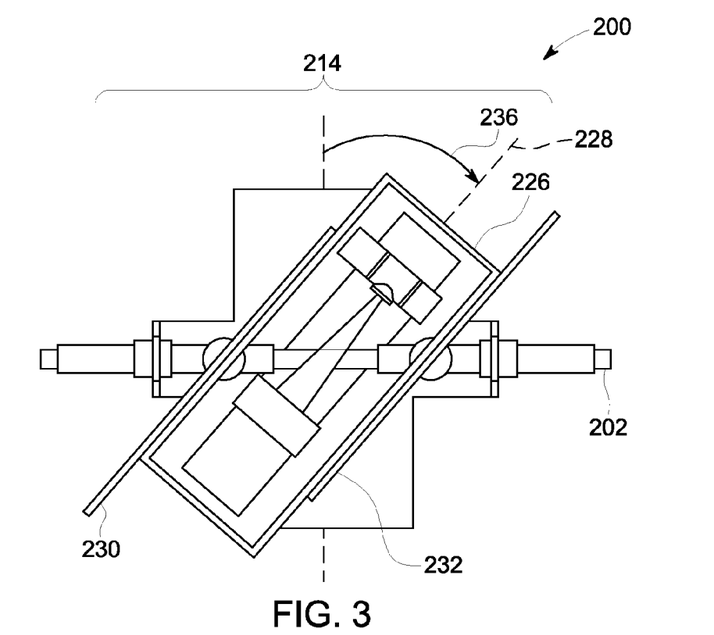
FIG. 3 depicts the exemplary inspection system of FIG. 2 in a second orientation.
Figure 4:
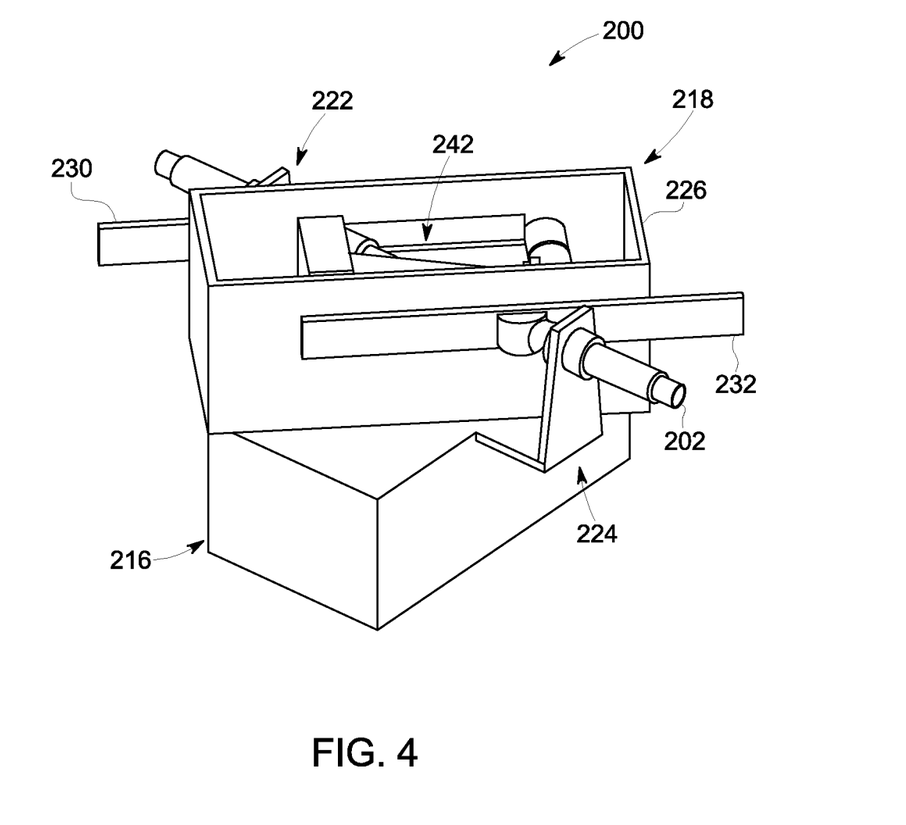
FIG. 4 depicts a side, perspective view of the exemplary inspection system of FIGS. 2 and 3.

FIGS. 2, 3, and 4 depict another exemplary inspection system 200 for inspecting an asset 202. In FIG. 2, the inspection system 200 includes a containment apparatus 214 with a support structure 216 and an enclosure 218 that moves relative to the support structure 216 and, in one example, relative to the asset 202 that is secured therein. The support structure 216 includes a base assembly 220 and a pair of support members (e.g., a first support member 222 and a second support member 224) on either side of the enclosure 218. The enclosure 218 includes a housing 226 with a longitudinal axis 228 on which the elements of the inspection device 204 can align. A pair of translating baffles (e.g., a first translating baffle 230 and a second translating baffle 232) secure to the housing 226. In one embodiment, the housing 226 can rotate relative to the position of the asset 202, as generally indicated by the numeral 234.

The support members 222, 224 are in position to secure and stabilize the asset 202 for imaging. These elements also permit the asset 202 to translate, or index, across the housing 226 from one side of the housing 226 to the other side of the housing 226. Indexing exposes different portions of the asset 202 inside of the housing 226 to radiation the inspection device 204 generates. The amount of translation can vary. When the focus of inspection is on one or more features-of-interest (e.g., features-of-interest 112 of FIG. 1), the amount the asset moves in the direction of travel, or the increment of the index, can correspond to the position of each feature-of-interest on the asset 202.

Rotation 234 changes the orientation of the housing 226 relative to the asset 202. The illustration of FIG. 2 shows the housing 226 in a first orientation, in which the longitudinal axis 228 is substantially orthogonal to the direction of travel of the asset 202. During operation, actuation of the housing 226 can increase and/or decrease the angular relationship between the longitudinal axis 228 and the asset 202. The selected angular relationship corresponds to the angle of the image that the inspection system captures and/or the orientation of the feature-of-interest inside of the image.

FIG. 3 illustrates the housing 226 in a second orientation after rotation through an inspection angle 236, which defines the angular displacement of the housing 226. In one example, the inspection angle 236 can vary by ±45°, although this disclosure contemplates configurations of the containment apparatus 214 in which the inspection angle 236 can encompass more and/or less angular displacement. The amount of variation in the inspection angle 236 may depend, in part, on certain aspects of the asset 202 that is under inspection, e.g., dimensions of the asset 202, position of the feature-of-interest (e.g., the feature-of-interest 112 (FIG. 1), location of possible anomalies, characteristics of the possible anomalies, technical specifications, industry standards, and combinations thereof. Other factors may include, for example, acceptable dimensions for the footprint of the inspection system 200 and similar peripheral factors that can place constraints on the overall dimensions and operation of the inspection system 200.

As also shown in FIG. 3, the housing 226 and the translating baffles 230, 232 engage one another to allow relative movement therebetween. The translating baffles 230, 232 can, in one example, slidingly engage features on the housing 226, e.g., features on the outside surface of the housing 226. In one example, the translating baffles 230, 232 affix to the support members 222, 224 in a manner that permits the translating baffles 230, 232 to rotate and/or translate, e.g., translate along the longitudinal axis 228. Such engagement between the support members 222, 224, the housing 226, and the translating baffles 230, 232 permits rotation of the housing 226 to various orientations (e.g., the first orientation (FIG. 2) and the second orientation (FIG. 3)) while also maintaining sufficient contact between the translating baffles 230, 232 to prevent radiation from leaking out of the housing 226.

FIG. 4 illustrates a side, perspective view of the inspection system 200 with the housing 226 in its second orientation. As shown in FIG. 4, the translating baffles 230, 232 cover an opening 242 in the housing 226 that exposes the interior of the housing 226 to the surrounding environment. The opening 242 permits the asset 202 to travel through the walls of the housing 226 into position in the path of radiation. Examples of the opening 242 can have various form factors, e.g., the slot shown in FIG. 4 and/or other shapes and configurations. The form factor should have dimensions and features that permit angular displacement sufficient for the housing 226 to rotate during inspection of the asset 202. The form factor can also be sized and configured for the opening 242 to receive a portion of the support members 222, 224 wherein such configuration may cause part of the support members 222, 224 to extend into the interior of the housing 226.

Figure 5:
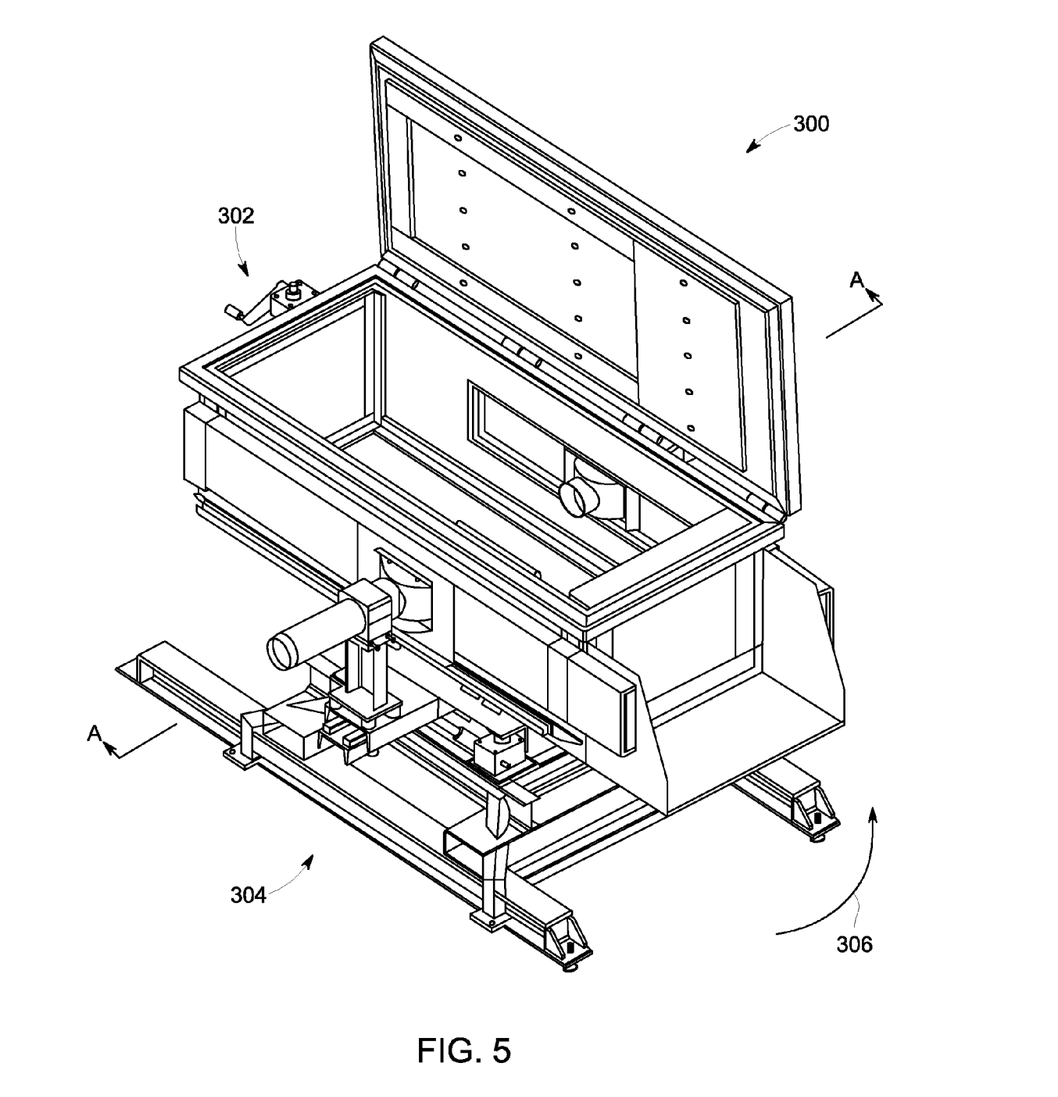
FIG. 5 depicts a perspective view of an example of a containment apparatus.

FIG. 5 illustrates an exemplary containment apparatus 300 that reduces exposure to radiation to the surrounding environment. The containment apparatus 300 includes an enclosure 302 and a support structure 304. In one embodiment, and as discussed in the text below, elements of the enclosure 302 work in conjunction with elements of the support structure 304 to form a structure that is substantially impenetrable to radiation. The combination of elements, however, allows the enclosure 302 to move relative to the support structure 304. In one example, the enclosure 302 sits on a portion of the support structure 304 that is equipped to rotate the enclosure 302, as generally identified by the numeral 306. Thus, when a portion of an asset that is under inspection is in position inside of the enclosure 302 for imaging, the enclosure 302 can change position relative to the asset to capture images at different angles.

Figure 6:
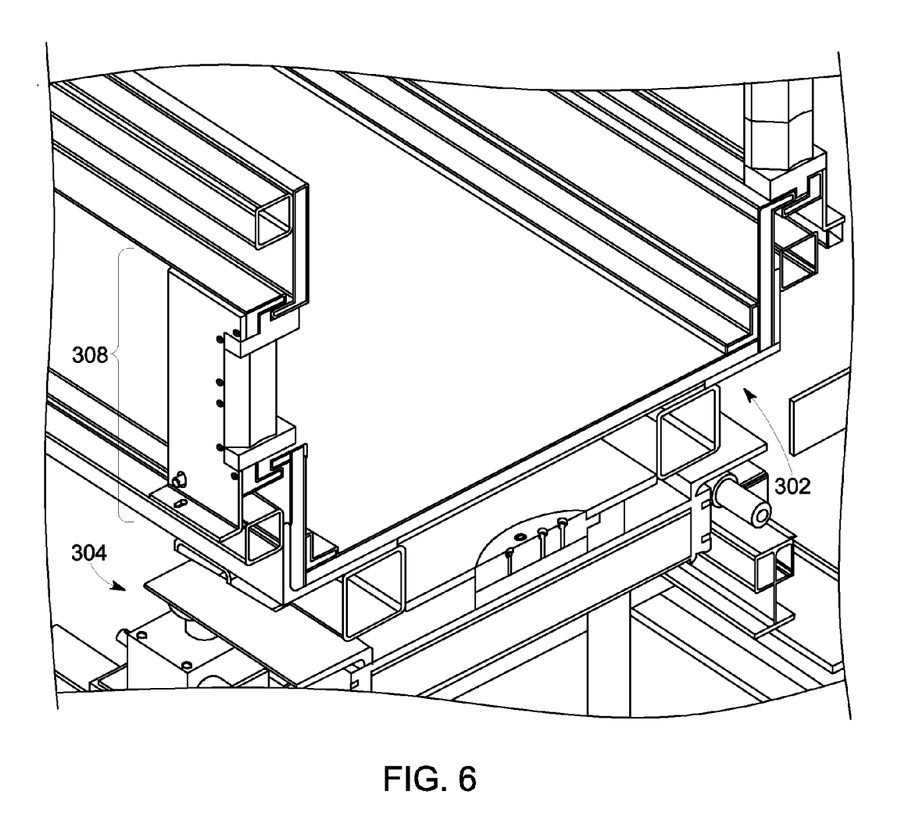
FIG. 6 depicts a cross-section of the containment apparatus of FIG. 5 taken along line A-A.

FIG. 6 shows a cross-section of the containment apparatus 300 taken along line A-A of FIG. 5. This figure shows the integration of the enclosure 302 and the support structure 304 at the point of penetration of an asset into the enclosure 302. In one embodiment, the containment apparatus 300 includes an integrated section 308 where the structure of the enclosure 302 integrates with the structure of the support structure 304. Construction of the integrated section 308 allows the enclosure 302 to rotate without exposing the surrounding environment to the radiation inside of the enclosure 302.

Details of the enclosure 302 and the support structure 304 follow below. These details set forth and describe one exemplary set of elements, some of which embody and are found in the integrated section 308. Collectively, configurations of these elements reduce, and in many cases, eliminate pathways through which radiation could escape from the interior of the enclosure through the point of penetration of the asset. In addition, material selection and composition for one or more of these elements is likewise provided relying in part on properties of such materials that make the elements impenetrable to radiation.

Figure 7:
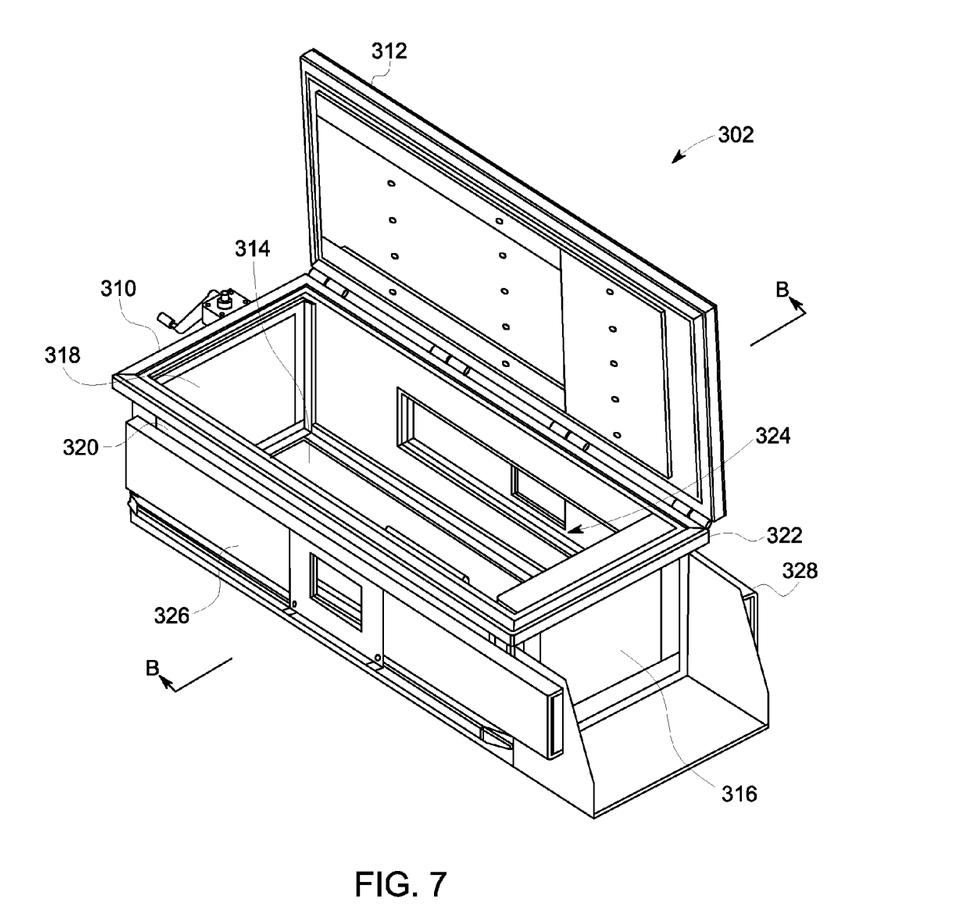
FIG. 7 depicts a perspective view of an enclosure for use in an inspection system.
Figure 8:
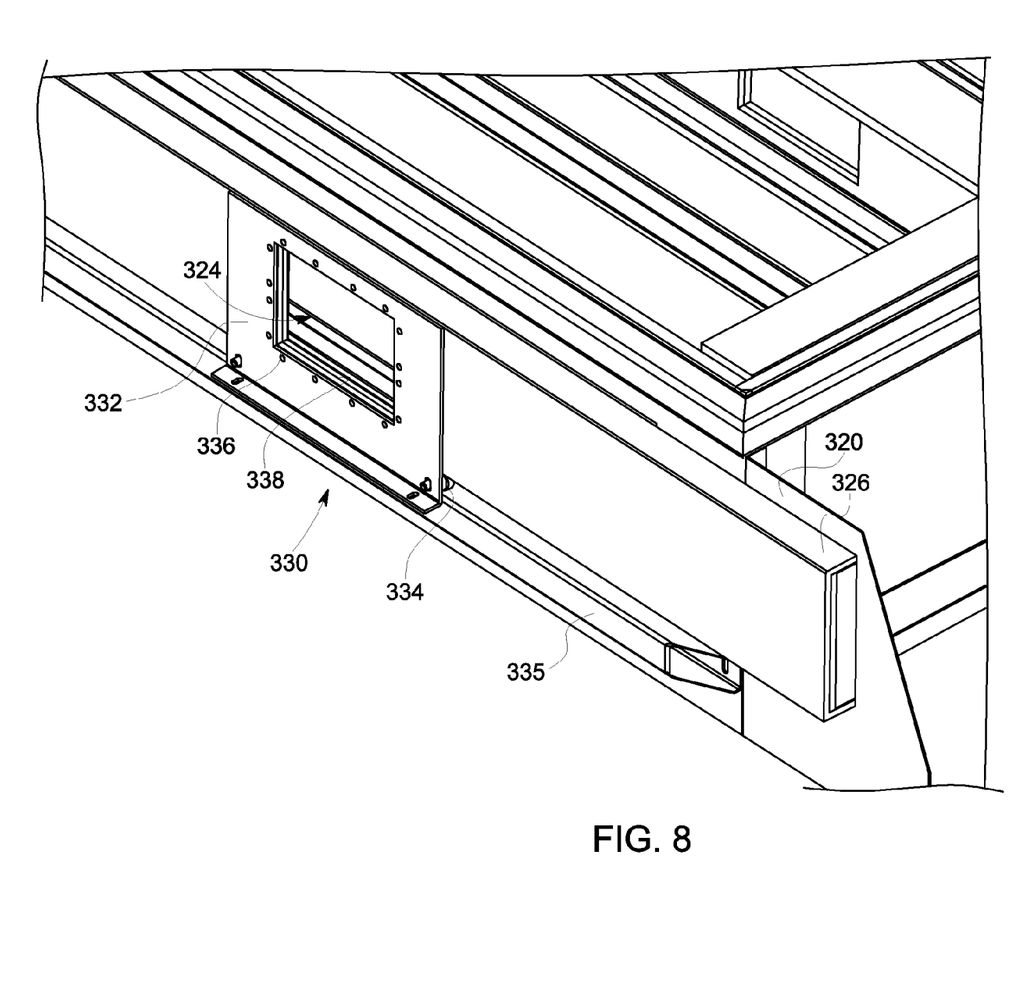
FIG. 8 depicts a detail view of a portion of the enclosure of FIG. 7.
Figure 9:
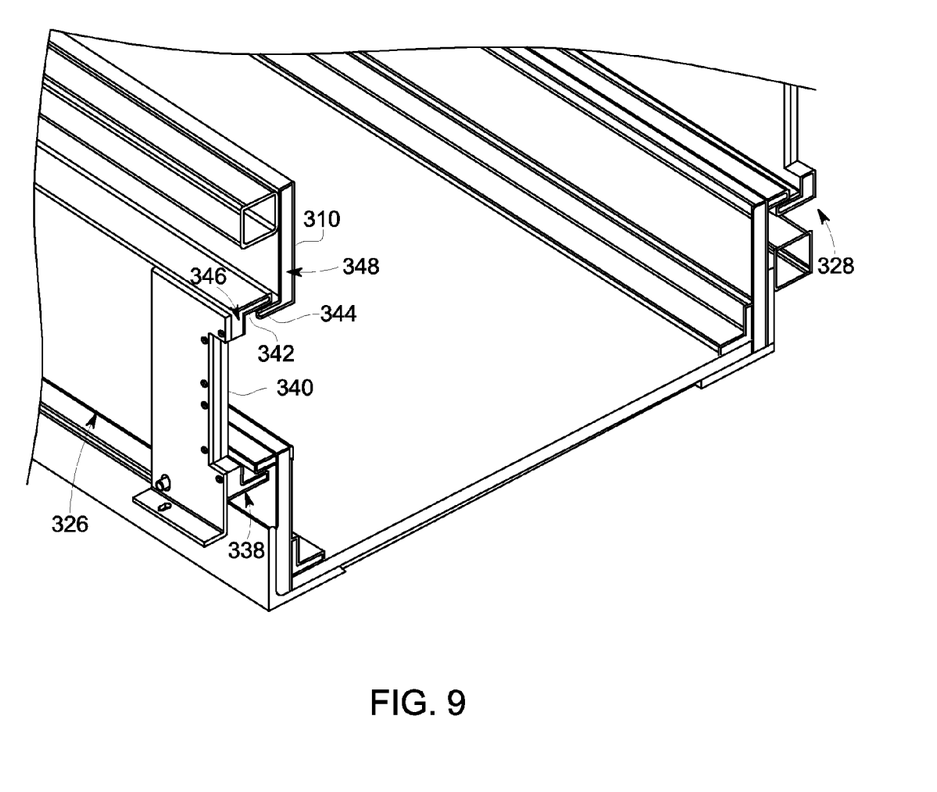
FIG. 9 depicts a cross-section view of the enclosure of FIG. 7 taken along line B-B.

FIGS. 7, 8, and 9 depict, in various views, the enclosure 302 that can house the inspection devices of the present disclosure. In FIG. 7, the enclosure 302 has a housing 310 having a top 312 and a bottom 314, a front wall 316, a back wall 318, and opposing side walls (e.g., a first side wall 320 and a second side wall 322) with an aperture 324 that penetrates therethrough. The enclosure 302 also includes a pair of translating baffles (e.g., a first translating baffle 326 and a second translating baffle 328) that secure to, respectively, the first side wall 320 and the second side wall 322.

As best shown in FIG. 8, a baffle support assembly 330 affixes to the outside surface of the translating baffles 326, 328. The baffle support assembly 330 includes a plate 332 and one or more rollers 334 that engage a rail 335 disposed on the outside of the housing 310. A first opening 336 in the plate 332 aligns with a second opening 338 in the translating baffles 326, 328 to provide access to the interior of the housing 310. In one embodiment, an asset (not shown) passes through the first opening 336, the second opening 338, and the aperture 324 to locate the portion of the asset that will be subject to radiation. In its present form, i.e., not mounted to a support structure, the translating baffles 326, 328 can slide along the opposing side walls 320, 322.

FIG. 9 illustrates a cross-section of the enclosure 302 taken along line B-B of FIG. 5. This view shows an exemplary construction of the housing 310 and the translating baffles 326, 328 that promotes effective containment of radiation inside of the housing 310. In one embodiment, the translating baffles 326, 328 have a C-shape profile 338 with an upright portion 340 and legs 342 that extend therefrom. The legs 342 extend over at least a portion of a protrusion 344, which extends from the outside surface of the housing 310 forming a lip or shelf. In one example, the protrusion 344 circumscribe the periphery of the aperture 324, creating a substantially continuous feature that overlaps with the legs 342.

Construction of the housing 310 and the translating baffles 326, 328 can include various layers of materials, e.g., steel, lead, and other materials that prevent penetration of radiation. In the present example, the translating baffles 326, 328 have a first layered structure 346 and the housing 310 has a second layered structure 348, the combination of which collectively exhibit properties that make the walls (e.g., the walls 312, 314, 316, 318, 320, 322) of the enclosure 302 impenetrable to radiation. Each of the layered structures 346, 348 can comprise a plurality of individual layers of different materials, e.g., combinations of steel and lead in quantities and thicknesses sufficient to prevent radiation from penetrating through the walls. In one example, one or both of the layered structures 346, 348 comprise a single layer of material, which can comprise lead and/or steel, as well as other combinations, derivations, and formulations of materials with properties that effectively prevent penetration by radiation through the walls of the enclosure 302.

Figure 10:
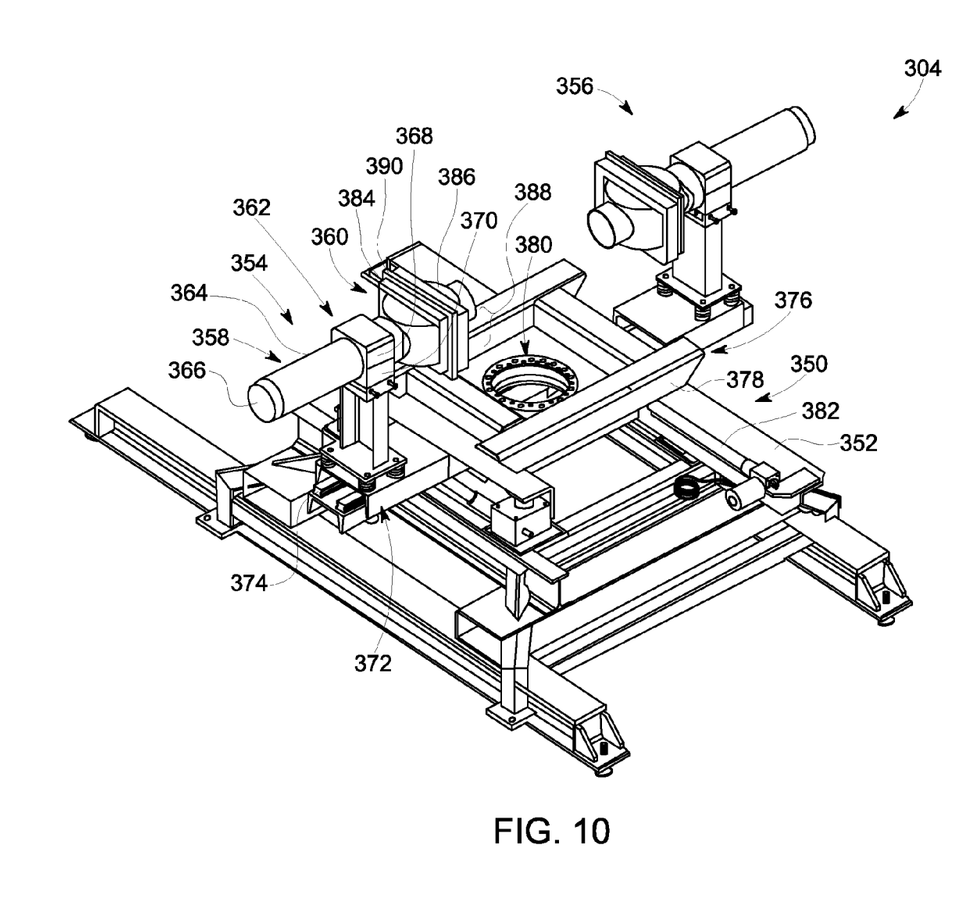
FIG. 10 depicts a perspective view of a support structure for use in an inspection system.
Figure 11:
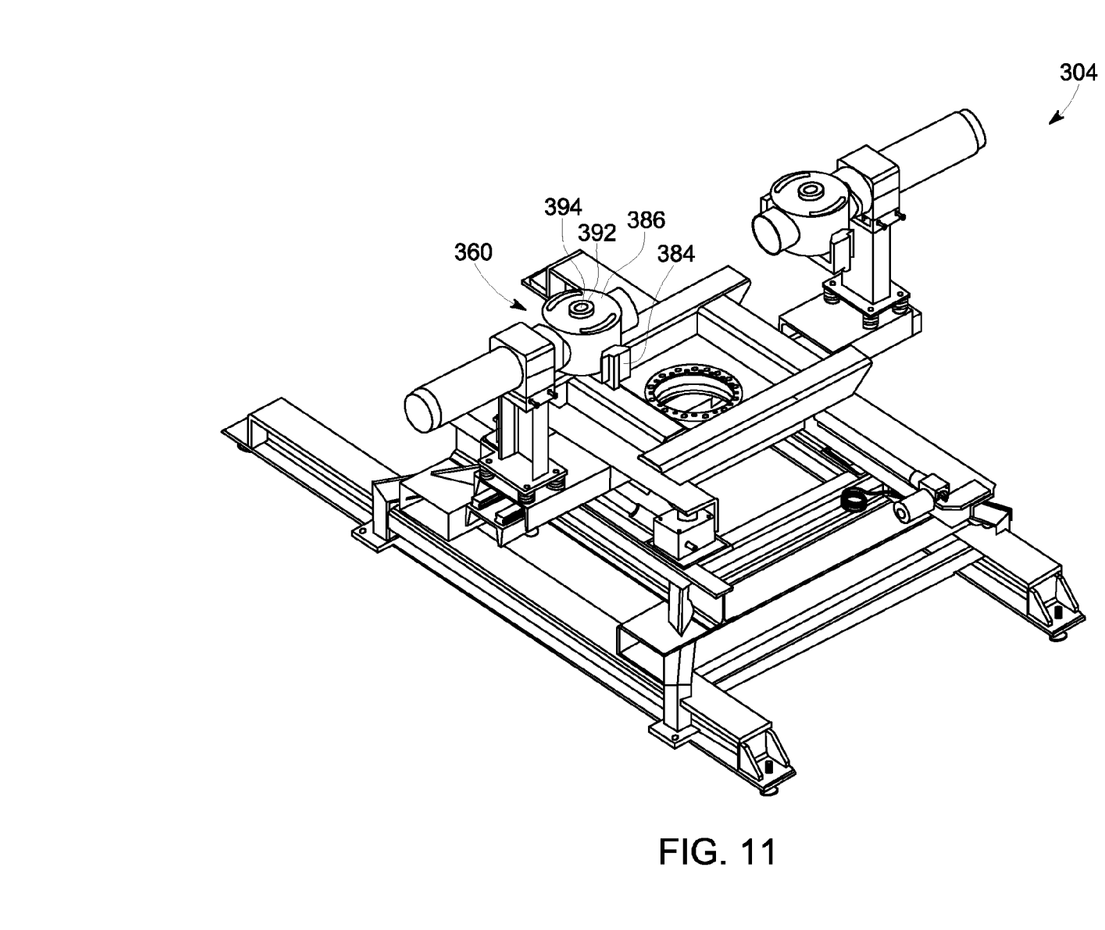
FIG. 11 depicts the support structure of FIG. 10 with parts removed for clarity.
Figure 12:
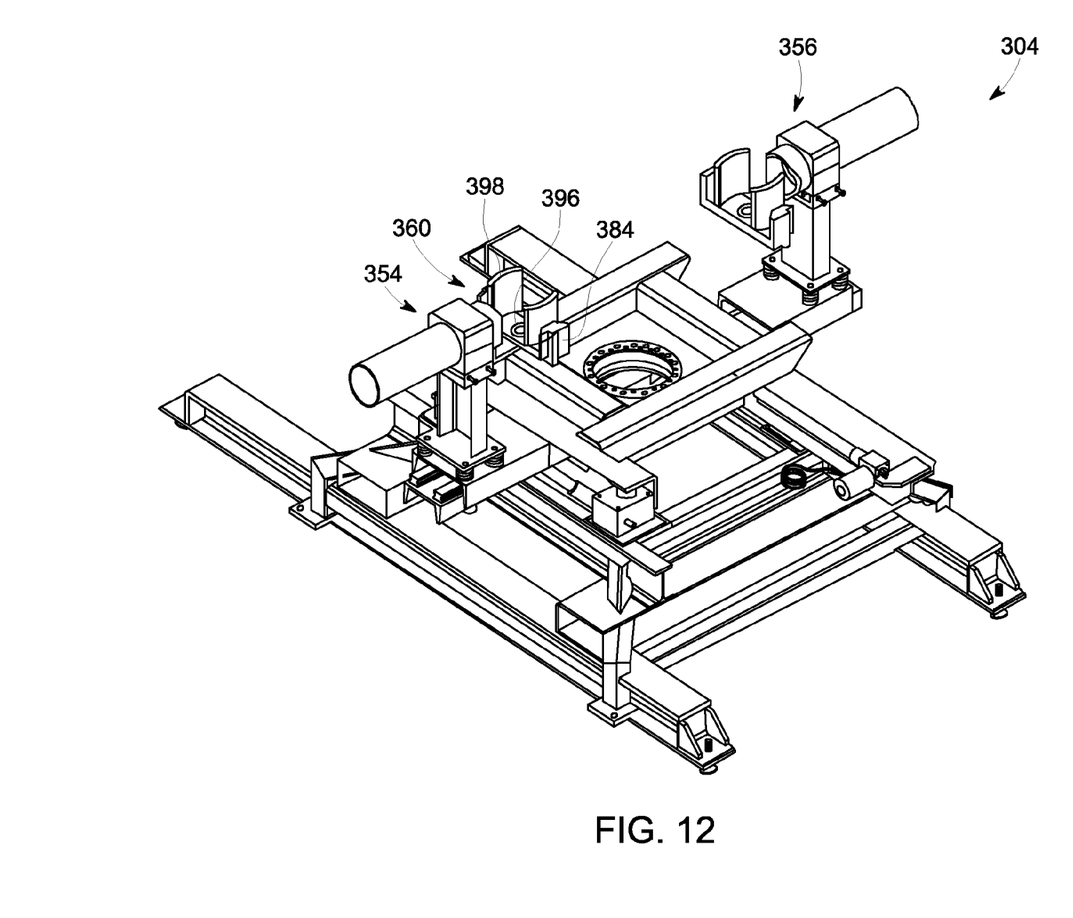
FIG. 12 depicts the support structure of FIG. 10 with parts removed for clarity.
Figure 13:
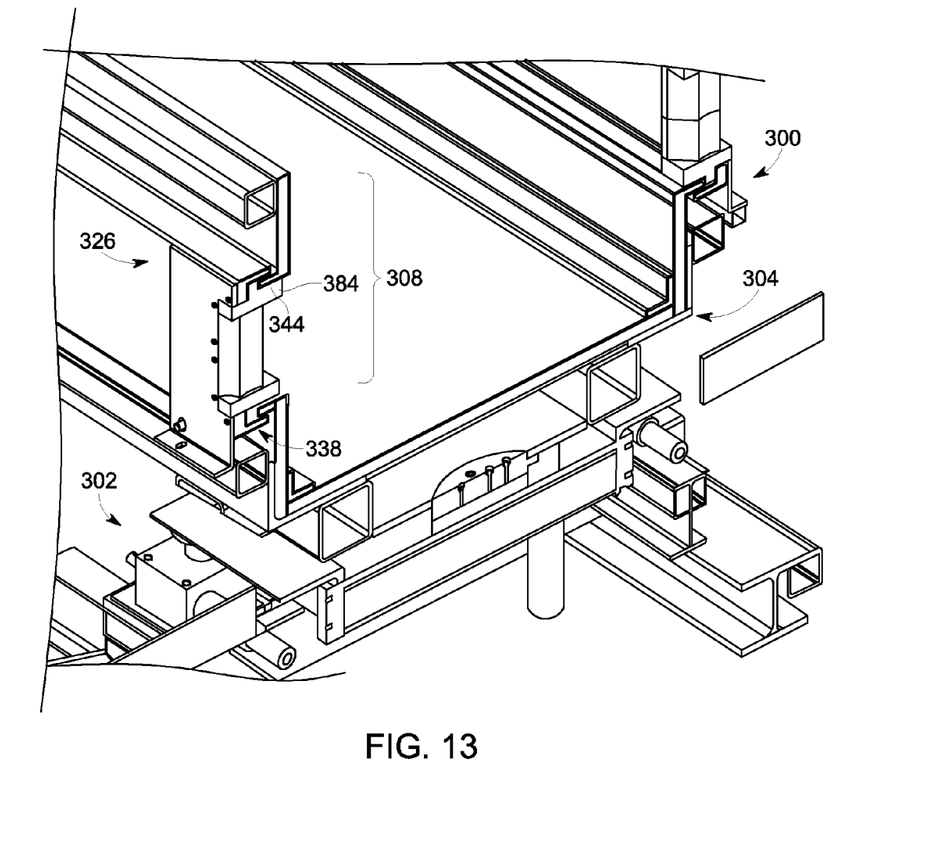
FIG. 13 depicts the cross-section view of the exemplary containment apparatus of FIG. 6.

FIGS. 10, 11, and 12 depict an example of the support structure 304. In FIG. 10, the support structure 304 includes a frame 350 having various frame members, generally identified by the numeral 352. The frame members 352 can comprise steel and/or other materials (e.g., composites and alloys) with physical properties sufficient to support the elements of the containment apparatus. Examples of the frame 350 can also incorporate leveling feet or pads, castors, wheels, and other elements to facilitate installation and set-up of the support structure 304 for operation as part of the containment apparatus 300.

The support structure 304 has a pair of support members (e.g. a first support member 354 and a second support member 356) with a sleeve member 358, a pivot member 360, and a clamp device 362. The sleeve member 358 can include one or more elongated tubes or pipes. In the present example, the sleeve member 358 has an outer sleeve 364 and an inner sleeve 366 disposed in the outer sleeve 364. The inner sleeve 366 has an interior dimension (e.g., a diameter) sufficient to receive an asset (not shown). The clamp device 362 secures the sleeve member 358, providing in one example a clamping force on the outer surface of the inner sleeve 366. The clamping force prevents movement of the sleeve member 358, e.g., as the asset traverses through the inner sleeve 366. In one example, the clamp device 362 can include an upper piece 368 and a lower piece 370 that work together to apply the clamping force about the periphery of the sleeve member 358.

In one embodiment, the clamp device 362 secures to a translating base 372 that includes one or more linear slides 374 on which the translating base 372 can move. The movement of the translating base 372 can change the position and/or increase and decrease the distance between the first support member 354 and the second support member 356. The support structure 304 also includes a rotatable base assembly 376 comprising, in one example, a number of frame members 378 and a bearing assembly 380. An actuator 382 couples with the rotatable base assembly 376. Examples of the actuator 382 can include pneumatic actuators, drive and lead screw assemblies, and similar devices that can generate a driving force that moves the rotatable base assembly 376. In one embodiment, the driving force is sufficient to cause the rotatable base assembly 376 to rotate and, in one construction of the containment apparatus 300, the driving force is large enough to accommodate the weight of the enclosure 302 that is disposed on the rotatable base assembly 376. In one embodiment, rotation of the rotatable base assembly 376 will change the position of one or more of the first support member 354 and the second support member 326.

The pivot member 360 can include an outer bearing component 384 that surrounds an inner sleeve component 386. The outer bearing component 384 can rotate about the inner sleeve component 386. In one example, the outer bearing component 384 has bifurcated construction 388 with an upper bearing component and a lower bearing component. A ridge feature 390 protrudes from the outer bearing component 384, circumscribing the upper bearing component and the lower bearing component.

As best shown in FIG. 11, the pivot member 360 can include an upper bearing 392 that installs on a first boss 394 found on the inner sleeve component 386. Part of the bifurcated construction 388 of the outer bearing component 384 can include a complimentary bore of diameter sufficient to receive the upper bearing 392. In FIG. 12, the pivot member 360 is shown to also include a lower bearing 396 seated in position in part of the outer bearing component 384 and a lining 398, which can comprise lead and reside inside and proximate the peripheral wall of the inner sleeve component 386. Although not shown in FIG. 12, in one example, the lower bearing 396 installs onto a second boss found on the inner sleeve component 386. Together the upper bearing 392 (FIG. 11) and the lower bearing 396 facilitate rotation of the outer bearing component 384 on the first support member 354 and the second support member 356.

FIG. 12 illustrates the cross-section of the containment apparatus 300 shown in FIG. 6. This figure shows the integration of the outer bearing component 384, the C-shaped profile 338, and the protrusion 344 in the integrated section 308. The combination of these elements form a labyrinth or tortuous pathway that prevents radiation from leaking around the periphery of the pivot element (e.g., pivot member 360 of FIG. 10). During rotation of the enclosure 302, the housing 310 can translate relative to the translating baffle 326 and the outer bearing component 384. However, during this translation, the integrity of the integrated section 308 remains, thereby preventing radiation from escaping from the interior of the housing 310.

Figure 14:
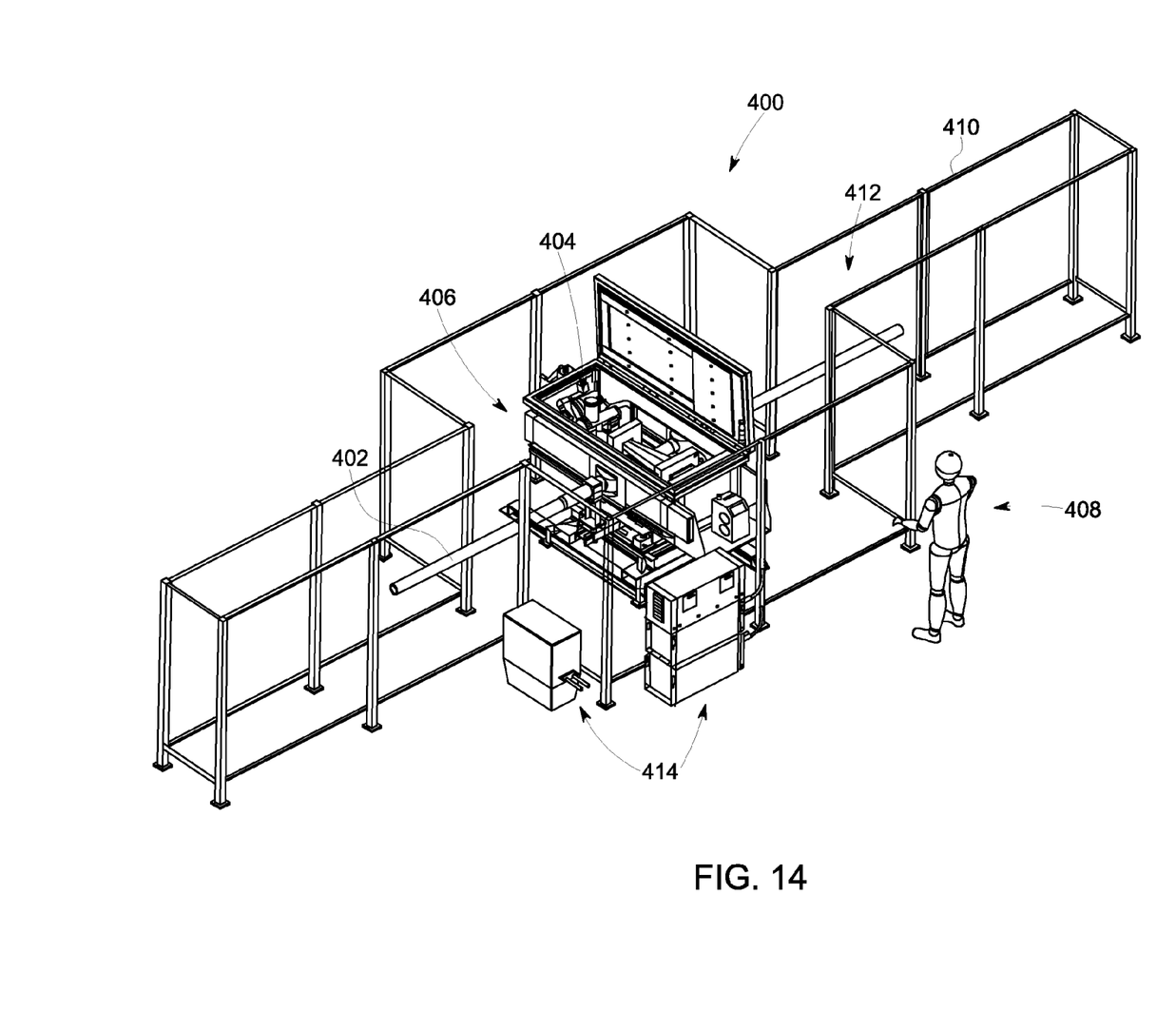
FIG. 14 depicts a perspective view of an exemplary inspection system that includes the containment apparatus of FIG. 5.

FIG. 14 depicts another exemplary inspection system 400 for imaging a portion of an asset 402. The inspection system 400 includes an inspection device 404 and a containment apparatus 406 which surrounds the inspection device 404 to prevent exposure to radiation by an operator 408. The inspection system 400 includes a barrier 410 that forms a safety zone 412 about the containment apparatus 406. In one embodiment, the inspection system 400 can include one or more peripheral devices 414 to operate the inspection device 404, to provide actuation of the containment apparatus 406 to change the angles of the images the inspection device 404 captures of the asset 402, as well as to offer other functionality (e.g., power, imaging processing, etc.) commonly to similar types of the inspection system 400.

As used herein, an element or function recited in the singular and proceeded with the word "a" or "an" should be understood as not excluding plural said elements or functions, unless such exclusion is explicitly recited. Furthermore, references to "one embodiment" of the claimed invention should not be interpreted as excluding the existence of additional embodiments that also incorporate the recited features.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An apparatus for inspecting an asset, the apparatus comprising:
    a support structure comprising a base assembly that can rotate, the support structure having support members that hold the asset in position for inspection;
    a housing disposed on the base assembly, the housing having a first side wall and a second side wall, the first side wall and the second side wall having an aperture exposing the interior of the housing and through which the asset can penetrate the housing for exposure to radiation; and
    a pair of translating baffles engaging the first side wall and the second side wall of the housing,
    wherein the translating baffles and the housing move relative to the one another in response to rotation of the base assembly, and
    wherein the translating baffles and the housing maintain engagement with one another to form an integrated section in combination with the support members on the first wall and the second wall proximate the asset.

2. The apparatus of claim 1, further comprising a baffle support assembly secured to the translating baffles, the baffle support assembly comprising a roller that engages a rail disposed on the outside of the housing.

3. The apparatus of claim 1, further comprising a pivot member coupled to the support members and integrated with the housing and the translating baffles at the integrated section.

4. The apparatus of claim 3, wherein the translating baffles are secured to the pivot members.

5. The apparatus of claim 1, wherein the housing can rotate through an inspection angle of 45° or more.

6. The apparatus of claim 1, wherein the translating baffles comprise a C-shaped profile that engages a protrusion on the housing, the protrusion circumscribing the periphery of the aperture.

7. The apparatus of claim 1, wherein the translating baffles comprise lead.

8. The apparatus of claim 1, wherein the housing comprises lead.

9. The apparatus of claim 1, further comprising an outer bearing component that surrounds the asset and engages each of the housing and the translating baffles in the integrated section.

10. The apparatus of claim 9, further comprising a lining radially interior to the outer bearing component, wherein the outer bearing component and the lining comprise lead.

11. A containment apparatus for housing a radiation source and a detector, said containment apparatus comprising:
   a support structure comprising an actuator; and
   an enclosure coupled to the actuator, the enclosure comprising a housing with an aperture on opposing side walls and a pair of translating baffles on the outside of the housing forming an integrated section with the housing about the apertures,
   wherein the translating baffles and the housing move relative to one another in response to rotation of the base assembly.

12. The containment apparatus of claim 11, further comprising a support member on either side of the housing, wherein the support member comprises a pivot member that engages the housing and the translating baffles to permit an asset to penetrate therethrough.

13. The containment apparatus of claim 11, wherein the translating baffles and the housing comprise lead in an amount sufficient to retain radiation from the radiation source inside of the housing.

14. The containment apparatus of claim 11, wherein housing rotates relative to the asset.

15. The containment apparatus of claim 11, wherein the translating baffles are secured to the support structure.

16. An inspection system for generating images of an asset, said inspection system comprising:
   an inspection device comprising a detector element sensitive to radiation from a radiation source;
   an enclosure surrounding the inspection device, the enclosure comprising a housing and a pair of translating baffles that engage the housing on opposing side walls; and
   a support structure supporting the enclosure, the support structure comprising a pivot element forming an integrated section with the translating baffles and the housing through which the asset passes from one of the opposing side walls to other opposing side wall,
   wherein the translating baffles and the housing move relative to one another when the housing changes orientation from a first orientation to a second orientation, and
   wherein the translating baffles, the housing, and the pivot member maintain engagement with one another at the integrated section in each of the first orientation and the second orientation proximate the asset.

17. The inspection system of claim 16, wherein the housing rotates relative to the asset.

18. The inspection system of claim 16, wherein the housing translates relative to the translating baffles.

19. The inspection system of claim 18, wherein the translating baffles couple with an outer bearing component of the pivot element, and wherein the outer bearing component comprises a ridge that integrates with the translating baffles and the housing in the integrated section.

20. The inspection system of claim 16, wherein the translating baffles and the housing comprise lead in an amount sufficient to retain radiation from the radiation source inside of the housing.

\* \* \* \* \*